United States Patent
Wang et al.

(10) Patent No.: US 9,000,239 B2
(45) Date of Patent: *Apr. 7, 2015

(54) METHODS FOR PRODUCING 1-CHLORO-3,3,3-TRIFLUOROPROPENE FROM 2-CHLORO-3,3,3-TRIFLUOROPROPENE

(71) Applicant: Honeywell International Inc., Morristown, NJ (US)

(72) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 98 days.

This patent is subject to a terminal disclaimer.

(21) Appl. No.: 13/804,656

(22) Filed: Mar. 14, 2013

(65) Prior Publication Data

US 2013/0310614 A1    Nov. 21, 2013

Related U.S. Application Data

(60) Provisional application No. 61/647,060, filed on May 15, 2012.

(51) Int. Cl.

| | | |
|---|---|---|
| *C07C 17/25* | (2006.01) | |
| *C07C 17/087* | (2006.01) | |
| *C07C 17/358* | (2006.01) | |
| *C07C 17/35* | (2006.01) | |
| *C07C 21/18* | (2006.01) | |
| *C07C 21/22* | (2006.01) | |
| *C07C 17/383* | (2006.01) | |

(52) U.S. Cl.
CPC .............. *C07C 17/35* (2013.01); *C07C 17/358* (2013.01); *C07C 17/087* (2013.01); *C07C 17/25* (2013.01); *C07C 17/383* (2013.01); *C07B 2200/09* (2013.01)

(58) Field of Classification Search
USPC .......................................... 570/151, 154, 233
See application file for complete search history.

(56) References Cited

U.S. PATENT DOCUMENTS

| | | | |
|---|---|---|---|
| 4,480,121 A * | 10/1984 | Klun et al. .................. 560/206 |
| 4,554,391 A * | 11/1985 | Klun et al. .................. 570/231 |
| 5,710,352 A | 1/1998 | Tung | |
| 6,844,475 B1 | 1/2005 | Tung et al. | |
| 7,109,386 B2 * | 9/2006 | Mathieu .................. 570/161 |
| 7,829,747 B2 | 11/2010 | Wang et al. | |
| 8,058,486 B2 | 11/2011 | Merkel et al. | |
| 8,653,310 B2 * | 2/2014 | Zhai et al. .................. 570/154 |
| 2009/0043136 A1 | 2/2009 | Wang et al. | |
| 2009/0270661 A1 | 10/2009 | Wang et al. | |
| 2010/0056657 A1 * | 3/2010 | Chen et al. .................. 521/98 |
| 2010/0152504 A1 * | 6/2010 | Hulse et al. .................. 570/151 |
| 2011/0201853 A1 | 8/2011 | Tung et al. | |
| 2011/0218369 A1 | 9/2011 | Elsheikh et al. | |
| 2011/0224465 A1 | 9/2011 | Merkel et al. | |
| 2011/0245549 A1 | 10/2011 | Merkel et al. | |
| 2012/0059199 A1 | 3/2012 | Pokrovski et al. | |
| 2012/0059200 A1 | 3/2012 | Pokrovski et al. | |
| 2013/0150633 A1 * | 6/2013 | Zhai et al. .................. 570/154 |

FOREIGN PATENT DOCUMENTS

| | | |
|---|---|---|
| WO | WO 2010095764 A1 * | 8/2010 |
| WO | 2011099605 A2 | 8/2011 |
| WO | WO 2011099605 A2 * | 8/2011 |

OTHER PUBLICATIONS

Hazeldine. J.Chem. Soc. 1952, pp. 3490-3498.*

* cited by examiner

*Primary Examiner* — Fereydoun G Sajjadi
*Assistant Examiner* — Medhanit Bahta
(74) *Attorney, Agent, or Firm* — Bruce O. Bradford

(57) ABSTRACT

The present invention provides processes for the production of HCFO-1233zd, 1-chloro-3,3,3-trifluoropropene, from the starting material, 2-chloro-3,3,3-trifluoropropene (HCFO-1233xf). In a first process, HCFO-1233zd is produced by the isomerization of HCFO-1233xf. In a second process, HCFO-1233zd is produced in a two-step procedure which includes (i) dehydrochlorination of HCFO-1233xf into trifluoropropyne; and (ii) hydrochlorination of the trifluoropropyne into HCFO-1233zd.

31 Claims, No Drawings

US 9,000,239 B2

METHODS FOR PRODUCING 1-CHLORO-3,3,3-TRIFLUOROPROPENE FROM 2-CHLORO-3,3,3-TRIFLUOROPROPENE

CROSS-REFERENCE TO RELATED APPLICATION

This application claims domestic priority to commonly owned, U.S. Provisional Patent Application Ser. No. 61/647,060, filed May 15, 2012, the disclosure of which is hereby incorporated herein by reference.

FIELD OF THE INVENTION

This invention relates to a process for preparing halogenated organic compounds, more particularly to a process for preparing halogenated olefins, and even more particularly to a process for producing 1-chloro-3,3,3-trifluoropropene (HCFO-1233zd).

BACKGROUND OF THE INVENTION

Chlorofluorocarbon (CFC) based chemicals have been widely used in industry in a variety of different applications including as refrigerants, aerosol propellants, blowing agents and solvents, among others. However, certain CFCs are suspected of depleting the Earth's ozone layer. Accordingly, more environmentally friendly substitutes have been introduced as replacements for CFCs. For example, 1,1,1,3,3-pentafluoropropane (HFC-245fa) is recognized as having favorable physical properties for certain industrial applications, such as foam blowing agents and solvents, and therefore is considered to be a good substitute for the CFCs previously used for these applications. Unfortunately, the use of certain hydrofluorocarbons, including HFC-245fa, in industrial applications is now believed to contribute to the global warming. Accordingly, more environmentally friendly substitutes for hydrofluorocarbons are now being sought.

The compound 1-chloro-3,3,3-trifluoropropene, also known as HCFO-1233zd or simply 1233zd, is a candidate for replacing HFC-245fa in some applications, including uses as blowing agents and solvents. 1233zd has a Z-isomer and an E-isomer. Due to differences in the physical properties between these two isomers, pure 1233zd(E), pure 1233zd(Z), or certain mixtures of the two isomers may be suitable for particular applications as refrigerants, propellants, blowing agents, solvents, or for other uses.

The prior art discloses various processes for making HCFO-1233zd. U.S. Pat. No. 5,710,352 discloses a vapor phase process for making 1,1,3,3,3-pentafluoropropane and HCFO-1233zd by reacting 1,1,1,3,3-pentachloropropane (HCC-240fa) with hydrogen fluoride in the presence of a fluorination catalyst. U.S. Pat. No. 6,844,475 discloses a low-temperature liquid phase process for making HCFO-1233zd by reacting 1,1,1,3,3-pentachloropropane (HCC-240fa) with hydrogen fluoride in the presence of a Lewis Acid catalyst or mixture of Lewis Acid catalysts. U.S. Pat. No. 7,829,747 discloses a vapor phase process for making HCFC-1233zd by dehydrofluorinating 3-chloro-1,1,1,3-tetra-fluoropropane (HCFC-244fa) in the presence of a dehydrofluorination catalyst. However, there remains a need for an economic means of producing HCFO-1233zd. The present invention satisfies this need among others. These documents are hereby incorporated herein by reference.

SUMMARY OF INVENTION

As provided herein, the instant invention is based on the use of 2-chloro-3,3,3-trifluoropropene (HCFO-1233xf) as starting raw material in the production of HCFO-1233zd, 1-chloro-3,3,3-trifluoropropene.

Thus, one embodiment of the invention is directed to a process for making 1-chloro-3,3,3-trifluoropropene (HCFO-1233zd) from 2-chloro-3,3,3-trifluoropropene (HCFO-1233xf) comprising:

(a) isomerization of HCFO-1233xf to yield HCFO-1233zd; or (b) a two-step procedure which comprises (i) dehydrochlorination of HCFO-1233xf into trifluoropropyne; and (ii) hydrochlorination of the trifluoropropyne into HCFO-1233zd; or (c) a combination of step (a) and step (b).

As set forth above, in one embodiment, HCFO-1233zd is produced through the isomerization reaction of HCFO-1233xf in a vapor phase reactor charged with an isomerization catalyst.

As set forth above, in another embodiment, HCFO-1233zd is produced through a two-step process, which comprises (i) the dehydrochlorination of HCFO-1233xf into trifluoropropyne ($CF_3C\equiv CH$) in a vapor phase reactor with or without an additional solid catalyst, and (ii) the hydrochlorination of the resultant trifluoropropyne into HCFO-1233zd in a vapor phase or a liquid phase reactor charged with a hydrochlorination catalyst.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

Disclosed are new manufacturing processes for making 1-chloro-3,3,3-trifluoropropene (HCFO-1233zd) from 2-chloro-3,3,3-trifluoropropene (HCFO-1233xf). As disclosed in U.S. Pat. No. 8,058,486, HCFO-1233xf can be produced through the fluorination of 1,1,2,3-tetrachloropropene (HCO-1230xa) and/or 1,1,1,2,3-pentachloropropane (HCC-240db) in a vapor phase reactor charged with a fluorination catalyst such as fluorinated chromia catalyst. This document is hereby incorporated herein by reference.

HCFO-1233zd production via direct isomerization of HCFO-1233xf:

In a first embodiment, HCFO-1233zd is produced through the direct isomerization of HCFO-1233xf in a vapor phase reactor charged with an isomerization catalyst. A stream of HCFO-1233xf is fed into an isomerization reactor which contains a suitable isomerization catalyst under conditions effective to convert at least a portion of the HCFO-1233xf into HCFO-1233zd.

The isomerization reaction may be conducted in any suitable reaction vessel or reactor, but it should preferably be constructed from materials which are resistant to corrosion such as nickel and its alloys, including Hastelloy, Inconel, Incoloy, and Monel or vessels lined with fluoropolymers. These may be single pipe or multiple tubes packed with an isomerization catalyst.

Three kinds of catalysts can be used for HCFO-1233xf isomerization reaction, which include 1) metal halides, 2) halogenated metal oxides, and 3) supported or unsupported transition metals. Suitable catalysts non-exclusively include fluorinated chromia, chromium fluoride, fluorinated alumina, aluminum fluoride, and carbon supported iron, cobalt, or nickel.

The isomerization reaction is preferably carried out under conditions to attain a HCFO-1233xf conversion of about 5% or higher, preferably about 20% or higher, and even more preferably about 50% or higher, and a HCFO-1233zd selectivity of about 50% or higher, preferably about 70% or higher, and more preferably about 90% or higher. Selectivity is calculated by number of moles of product (HCFO-1233zd) formed divided by number of moles of reactant consumed.

Useful isomerization reaction temperatures range from about 100° C. to about 600° C. Preferred temperatures range from about 200° C. to about 500° C., and more preferred temperatures range from about 300° C. to about 400° C. The reaction may be conducted at atmospheric pressure, super-atmospheric pressure or under vacuum. The vacuum pressure can be from about 5 torr to about 760 torr. Contact time of the HCFO-1233xf with the catalyst may range from about 0.5 seconds to about 120 seconds, however, longer or shorter times can be used.

The product stream from isomerization reactor may be fed directly into a suitable distillation operation. In other embodiments, the product stream is fed through an intermediate unit operation prior to being fed into the distillation column or is stored prior to being fed through the distillation column. In some embodiments, the distillation process yields substantially pure, or pure, separated product streams of 1233zd(Z) and 1233zd(E). Separated HCFO-1233xf may be recycled back into the isomerization reactor.

HCFO-1233zd production via a two-step process:

In a second embodiment, HCFO-1233zd is produced through a two-step process, which comprises (i) dehydrochlorination of HCFO-1233xf into trifluoropropyne, ($CF_3C{\equiv}CH$), in a vapor phase reactor with or without an additional solid catalyst, and (ii) hydrochlorination of the resultant trifluoropropyne into HCFO-1233zd in a vapor phase or a liquid phase reactor charged with a hydrochlorination catalyst.

In the first step of the two-step process, HCFO-1233xf is fed into a vapor phase reactor (dehydrochlorination reactor) under conditions effective to be dehydrochlorinated to make the desired intermediate trifluoropropyne. The dehydrochlorination reactor can either be non-catalytic or can contain a catalyst that can catalytically dehydrochlorinate HCFO-1233xf to make trifluoropropyne. Three kinds of catalysts can be used for HCFO-1233xf dehydrochlorination reaction, which include 1) metal halides, 2) halogenated metal oxides, and 3) metals and metal alloys.

The dehydrochlorination reaction is preferably carried out under conditions to attain a HCFO-1233xf conversion of about 1% or higher, preferably about 10% or higher, and even more preferably about 20% or higher, and a $CF_3C{\equiv}CH$ selectivity of about 50% or higher, preferably about 70% or higher, and more preferably about 90% or higher. Selectivity is calculated by number of moles of product ($CF_3C{\equiv}CH$) formed divided by number of moles of reactant consumed.

The reaction temperature for this embodiment ranges from about 200° C. to about 800° C., preferably from about 300° C. to about 600° C., and more preferably from about 400° C. to about 500° C. The reactor pressure ranges from about 0 psig to about 200 psig, preferably from about 10 psig to about 100 psig, and more preferably from about 20 to about 70 psig.

The dehydrochlorination reaction may be conducted in any suitable reaction vessel or reactor, but it should preferably be constructed from materials which are resistant to corrosion such as nickel and its alloys, including Hastelloy, Inconel, Incoloy, and Monel or vessels lined with fluoropolymers. These may be single pipe or multiple tubes. When no additional solid catalyst is present, the reactor is preferably constructed from Inconel alloys. Non-limiting examples of Inconel alloys include, but are not limited to, Inconel 600, Inconel 601, Inconel 617, Inconel 625, Inconel 690, and Inconel 718.

In general, the effluent from the dehydrochlorination reactor may be processed to achieve desired degrees of separation and/or other processing. Besides $CF_3C{\equiv}CH$ produced, the effluent generally contains HCl, unconverted HCFO-1233xf, and some by-products. Optionally but preferably, HCl is then recovered from the result of the dehydrochlorination reaction. Recovering of HCl is conducted by conventional distillation where it is removed from the distillate. Alternatively, HCl can be recovered or removed by using water or caustic scrubbers. When a water extractor is used HCl is removed as an aqueous solution. When caustic is used, HCl is removed from system as a chloride salt in aqueous solution.

After the recovery or removal of HCl, the organic stream may be sent to a distillation column for separation. $CF_3C{\equiv}CH$, collected from the overhead of the column, may be sent to next step for further reaction, while the bottom stream from reboiler may be sent to another distillation column to recover unconverted HCFO-1233xf. The recovered HCFO-1233xf may be sent back to dehydrochlorination reactor for recycle.

In the second step of this two-step process, HCl is reacted with $CF_3C{\equiv}CH$ formed in the first step in the presence of a hydrochlorination catalyst under conditions effective to facilitate a hydrochlorination reaction and to form a product stream comprising HCFO-1233zd. The effluent stream exiting reactor may optionally comprise additional components, such as un-reacted HCl, and unconverted $CF_3C{\equiv}CH$. The hydrochlorination process may be carried out in a vapor phase or a liquid phase.

In vapor-phase hydrochlorination, HCl is fed continuously through the catalyst bed. After a short time with only the HCl feed stream, $CF_3C{\equiv}CH$ is fed continuously through the catalyst bed at a ratio of about 1:2 to about 1:20 and preferably from about 1:4 to about 1:10 $CF_3C{\equiv}CH/HCl$ mole ratio.

The reaction between HCl and $CF_3C{\equiv}CH$ is carried out at a temperature from about 100° C. to about 500° C., preferably from about 200° C. to about 400° C.; and at a pressure of about 5 psig to about 200 psig (pounds per square inch gauge), preferably from about 20 psig to about 100 psig. Suitable vapor phase solid catalysts include, but are not limited to chromium, aluminum, cobalt, manganese, nickel and iron oxides, hydroxides, halides, oxyhalides, inorganic salts thereof and their mixtures. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes.

The catalyst may be supported on a substrate, such as on activated carbon, or may be unsupported or free-standing. In addition to activated carbon, useful catalyst supports include: alumina, fluorinated alumina, aluminum fluoride, alkaline earth metal oxides, fluorinated alkaline earth metal oxides, zinc oxide, zinc fluoride, tin oxide, and tin fluoride. Optionally but preferably, metal oxide catalysts are subject to halogenation treatment in hydrogen halide flow at sufficiently high temperatures prior to reaction. Halogenation treatments can include any of those known in the prior art, particularly those that employ HF, $F_2$, HCl, $Cl_2$, HBr, $Br_2$, HI, and $I_2$ as the halogenation source.

In liquid phase hydrochlorination, a liquid phase hydrochlorination catalyst is charged in a liquid form to a reactor and optionally activated with HF or $Cl_2$. A non-exhaustive list includes Lewis Acids, transition metal halides, Periodic Table Group IVb metal halides, Group Vb metal halides, and combinations thereof. Non-exclusive examples of liquid phase hydrochlorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase hydrochlorination catalysts are $SbCl_5$, $SbCl_3$, $SbF_5$, $SnCl_4$, $TaCl_5$, $TiCl_4$, $NbCl_5$, $MoCl_6$, $AlCl_3$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, and combinations thereof.

The activated catalyst is then heated to the desired reaction temperature of about 30° C. to about 200° C., preferably from about 50° C. to about 120° C.; and the pressure is kept between about 15 psig to about 200 psig, preferably from about 50 psig to about 175 psig. After a few minutes (e.g., less than 30, or 20, or 10, or 5) with only the HCl feed, a feed stream of $CF_3C{\equiv}CH$ is fed continuously through the catalyst at a ratio of about 1:2 to about 1:20, and preferably from about 1:4 to about 1:15 $CF_3C{\equiv}CH$/HCl mole ratio. If necessary, the catalyst can be kept activated by the continuous or batch addition of $Cl_2$ or a similar oxidizing agent.

The hydrochlorination reaction is preferably carried out to achieve a conversion of about 50% or more, preferably about 70% or more, and most preferably about 90% or more. The selectivity for HCFO-1233zd attained is preferably about 80% or more and most preferably about 90% or more.

The hydrochlorination is preferably carried out in a corrosion-resistant reaction vessel. Examples of corrosion-resistant materials are Hastelloy, Nickel, Incoloy, Inconel, Monel and fluoropolymer linings. The vessel may have a fixed catalyst bed, or contain liquid catalyst. If desired, inert gases such as nitrogen or argon may be employed in the reactor during operation. Optionally but preferably, the reactor effluent is fed to a caustic scrubber or to a distillation column or to an extractor to recover/remove the un-converted HCl to produce an acid-free organic product stream which is subject to further purification. Recovering of HCl is conducted by conventional distillation where it is removed from the distillate. Alternatively, HCl can be recovered or removed by using water or caustic scrubbers. When a water extractor is used HCl is removed as an aqueous solution. When caustic is used, HCl is removed from system as a chloride salt in aqueous solution.

The acid-free organic stream is then fed directly into a suitable distillation operation. In other embodiments, the product stream is fed through an intermediate unit operation prior to being fed into the distillation column or is stored prior to being fed through the distillation column. In some embodiments, the distillation process yields substantially pure, or pure, separated product streams of 1233zd(Z) and 1233zd(E). Recovered $CF_3C{\equiv}CH$ may be recycled back to the hydrochlorination reactor.

The following are examples of the invention, which are not to be construed as limiting.

EXAMPLE 1

HCFO-1233xf Isomerization over Fluorinated Chromia Catalyst

A Monel tube reactor (0.75 inch OD×0.625 inch ID×23.0 inches L) is charged with 20 ml of fluorinated chromia catalyst pellets. The reactor is heated by a 12 inch split tube furnace. A multi-point thermocouple, inserted through catalyst bed, is used to measure the temperature of catalyst bed. A 99.9% pure HCFO-1233xf feed is passed over this catalyst at a rate of 12 g/h. The reaction is conducted at 0.0 psig and at 350° C. The effluent is analyzed by an on-line GC to determine the performance of the catalyst. Based on the GC analysis after 10 hours on stream, it is determined that the reactor effluent comprises 49.9 GC area % of HCFO-1233xf, 32.5 GC area % of HCFO-1233zd(E), and 16.2 GC area % of HCFO-1233zd(Z).

EXAMPLE 2

HCFO-1233xf Dehydrochlorination in the Absence of Extra Solid Catalyst

An Inconel 625 tube reactor (0.75 inch OD×0.625 inch ID×23.0 inches L) is used without charging any additional solid catalyst. The reactor is heated by a 12 inch split tube furnace. A multi-point thermocouple, inserted through the reactor, is used to measure the process temperature. A 99.9% pure HCFO-1233xf feed is passed through the reactor at a rate of 12 g/h. The reaction is conducted at 70.0 psig and at 500° C. The effluent is analyzed by an on-line GC to the progress of the reaction. Based on the GC analysis after 10 hours on stream, it is determined that the reactor effluent comprises 70.9 GC area % of HCFO-1233xf, 25.8 GC area % of trifluoropropyne.

EXAMPLE 3

Trifluoropropyne Hydrochlorination Over Fluorinated Chromia Catalyst

A Monel tube reactor (0.75 inch OD×0.625 inch ID×23.0 inches L) is charged with 20 ml of fluorinated chromia catalyst pellets. The reactor is heated by a 12 inch split tube furnace. A multi-point thermocouple, inserted through catalyst bed, is used to measure the temperature of catalyst bed. The reactor is heated to desired set point in nitrogen flow. HCl flow (at a rate of 19 g/h) followed by trifluoropropyne flow (at a rate of 12 g/h) are then started. The mole ratio of HCl/trifluoropropyne is about 4/1. The reaction is conducted at 80.0 psig and at 320° C. The effluent is analyzed by an on-line GC to determine the performance of the catalyst. Based on the GC analysis after 10 hours on stream, it is determined that the reactor effluent comprises 6.9 GC area % of HCFO-1233xf, 69.2 GC area % of HCFO-1233zd (E), and 20.6 GC area % of HCFO-1233zd (Z).

As used herein, the singular forms "a", "an" and "the" include plural unless the context clearly dictates otherwise. Moreover, when an amount, concentration, or other value or parameter is given as either a range, preferable range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making 1-chloro-3,3,3-trifluoropropene (HCFO-1233zd) from 2-chloro-3,3,3-trifluoropropene (HCFO-1233xf) comprising:
   (a) isomerization of HCFO-1233xf to yield HCFO-1233zd;
   wherein the isomerization reaction of HCFO-1233xf is conducted in a vapor phase reactor charged with an isomerization catalyst comprising fluorinated chromia catalyst pellets; and
   wherein the isomerization reaction is carried out at 0.0 psig and at 350° C. to attain a HCFO-1233xf conversion of about 50%.

2. The process of claim 1, wherein the isomerization reaction is carried out under conditions to attain a HCFO-1233zd selectivity of about 70% or higher.

3. The process of claim 1, wherein the isomerization reaction is carried out under conditions to attain a HCFO-1233zd selectivity of about 90% or higher.

4. The process of claim 1, wherein the product stream from the isomerization reaction is further fed directly into a suitable distillation operation.

5. The process of claim 4, wherein the product stream from the isomerization reaction is further fed through an intermediate unit operation prior to being fed into the distillation column.

6. The process of claim 4, wherein the product stream from the isomerization reaction is further stored prior to being fed through the distillation column.

7. The process of claim 4, wherein the product stream from the distillation process yields separated product streams of 1233zd(Z) and 1233zd(E).

8. The process of claim 4, wherein the product stream from the distillation process further includes unreacted HCFO-1233xf which is recycled back into the isomerization reactor.

9. A process for the production of HCFO-1233zd, wherein the HCFO-1233zd is produced through a two-step process, which comprises
   (i) dehydrochlorination of HCFO-1233xf into trifluoropropyne in a vapor phase reactor optionally using a dehydrochlorination catalyst selected from the group consisting of, halogenated metal oxides, metals, metal alloys, and mixtures thereof;
   wherein the reaction is conducted at a temperature in the range of 200° C. to 800° C. solid, and
   (ii) hydrochlorination of the resultant trifluoropropyne into HCFO-1233zd in a vapor phase or a liquid phase reactor, charged with a hydrochlorination catalyst,
   wherein the hydrochlorination catalyst is selected from the group consisting of chromium, aluminum, cobalt, manganese, nickel and iron oxides, hydroxides, halides, oxyhalides, inorganic salts thereof and their mixtures.

10. The process of claim 9, wherein the dehydrochlorination reaction is a non-catalytic reaction.

11. The process of claim 9, wherein the dehydrochlorination reaction attains a HCFO-1233xf conversion of about 1% or higher.

12. The process of claim 9, wherein the dehydrochlorination reaction attains a HCFO-1233xf conversion of about 10% or higher.

13. The process of claim 9, wherein the dehydrochlorination reaction attains a HCFO-1233xf conversion of about 20% or higher.

14. The process of claim 9, wherein the dehydrochlorination reaction attains a HCFO-1233zd selectivity of about 50% or higher.

15. The process of claim 9, wherein the dehydrochlorination reaction attains a HCFO-1233zd selectivity of about 70% or higher.

16. The process of claim 9, wherein the dehydrochlorination reaction attains a HCFO-1233zd selectivity of about 90% or higher.

17. The process of claim 9, wherein the second step of the two-step process comprises the reaction of HCl with the trifluoropropyne formed in the first step in the presence of a hydrochlorination catalyst facilitates a hydrochlorination reaction and to form a product stream comprising HCFO-1233zd.

18. The process of claim 17, wherein the hydrochlorination process is carried out in the vapor phase.

19. The process of claim 18, wherein the HCl is fed continuously through the catalyst bed, and after a few minutes with only the HCl feed stream, the trifluoropropyne is also fed continuously through the catalyst bed, at a mole ratio of about 1:2 to about 1:20 of trifluoropropyne to HCl.

20. The process of claim 19, wherein the mole ratio of trifluoropropyne to HCl is from about 1:4 to about 1:10.

21. A process for making 1-chloro-3,3,3-trifluoropropene (HCFO-1233zd) from 2-chloro-3,3,3-trifluoropropene (HCFO-1233xf) comprising:
   a two-step procedure which comprises (i) dehydrochlorination of HCFO-1233xf into trifluoropropyne; and (ii) hydrochlorination of the trifluoropropyne into HCFO-1233zd;
   wherein the HCFO-1233zd is produced through a two-step process, which comprises:
   (i) dehydrochlorination of HCFO-1233xf into trifluoropropyne in a vapor phase reactor wherein the reaction is conducted at a temperature in the range of 200° C. to 800° C. and
   (ii) hydrochlorination of the resultant trifluoropropyne into HCFO-1233zd in a vapor phase or a liquid phase reactor, charged with a hydrochlorination catalyst;
   wherein the second step of the two-step process comprises the reaction of HCl with the trifluoropropyne formed in the first step in the presence of a hydrochlorination catalyst under conditions effective to facilitate a hydrochlorination reaction and to form a product stream comprising HCFO-1233zd; and
   wherein the hydrochlorination catalyst comprises a chromium (III) oxide selected from the group consisting of crystalline chromium oxide and amorphous chromium oxide.

22. A process for making 1-chloro-3,3,3-trifluoro-propene (HCFO-1233zd) from 2-chloro-3,3,3-trifluoropropene (HCFO-1233xf) comprising:

a two-step procedure which comprises (i) dehydrochlorination of HCFO-1233xf into trifluoropropyne; and (ii) hydrochlorination of the trifluoropropyne into HCFO-1233zd;

wherein the second step of the two-step process comprises the reaction of HCl with the trifluoropropyne formed in the first step in the presence of a hydrochlorination catalyst which facilitates a hydrochlorination reaction and to form a product stream comprising HCFO-1233zd;

wherein the hydrochlorination catalyst is selected from the group consisting of chromium, aluminum, cobalt, manganese, nickel and iron oxides, hydroxides, halides, oxyhalides, inorganic salts thereof and their mixtures; and wherein the hydrochlorination catalyst is supported on a substrate selected from the group consisting of activated carbon, alumina, fluorinated alumina, aluminum fluoride, alkaline earth metal oxides, fluorinated alkaline earth metal oxides, zinc oxide, zinc fluoride, tin oxide, and tin fluoride.

23. The process of claim 17, wherein the hydrochlorination process is carried out in the liquid phase.

24. The process of claim 23, wherein the liquid phase hydrochlorination catalyst is selected from the group consisting of Lewis Acids, transition metal halides, Periodic Table Group IVb metal halides, Group Vb metal halides, and combinations thereof.

25. The process of claim 23, wherein the liquid phase hydrochlorination catalyst is selected from the group consisting of antimony halides, tin halides, tantalum halides, titanium halides, niobium halides, molybdenum halides, iron halides, fluorinated chrome halides, fluorinated chrome oxides and combinations thereof.

26. The process of claim 23, wherein the liquid phase hydrochlorination catalyst is selected from the group consisting of $SbCl_5$, $SbCl_3$, $SbF_5$, $SnCl_4$, $TaCl_5$, $TiCl_4$, $NbCl_5$, $MoCl_6$, $AlCl_3$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, and combinations thereof.

27. The process of claim 23, wherein the hydrochlorination reaction is carried out in a manner to achieve a conversion of about 50% or more.

28. The process of claim 23, wherein the hydrochlorination reaction is carried out in a manner to achieve a conversion of about 70% or more.

29. The process of claim 23, wherein the hydrochlorination reaction is carried out in a manner to achieve a conversion of about 90% or more.

30. The process of claim 23, wherein the hydrochlorination reaction is carried out in a manner to achieve a selectivity for HCFO-1233zd of about 80% or more.

31. The process of claim 23, wherein the hydrochlorination reaction is carried out in a manner to achieve a selectivity for HCFO-1233zd of about 90% or more.

* * * * *